United States Patent
Lu et al.

(10) Patent No.: US 11,504,034 B2
(45) Date of Patent: *Nov. 22, 2022

(54) SYSTEMS AND METHODS FOR DETERMINING BLOOD PRESSURE OF A SUBJECT

(71) Applicant: VITA-COURSE DIGITAL TECHNOLOGIES (TSINGTAO) CO., LTD., Shandong (CN)

(72) Inventors: Ying Lu, Haikou (CN); Chuanmin Wei, Haikou (CN); Jiwei Zhao, Haikou (CN); Heng Peng, Haikou (CN); Ziming Deng, Haikou (CN); Zijian Huang, Haikou (CN); Zhiyong Wang, Haikou (CN)

(73) Assignee: VITA-COURSE DIGITAL TECHNOLOGIES (TSINGTAO) CO., LTD., Tsingtao (CN)

( * ) Notice: Subject to any disclaimer, the term of this patent is extended or adjusted under 35 U.S.C. 154(b) by 128 days.

This patent is subject to a terminal disclaimer.

(21) Appl. No.: 16/633,167

(22) PCT Filed: Jul. 27, 2017

(86) PCT No.: PCT/CN2017/094762
§ 371 (c)(1),
(2) Date: Jan. 23, 2020

(87) PCT Pub. No.: WO2019/019119
PCT Pub. Date: Jan. 31, 2019

(65) Prior Publication Data
US 2021/0153750 A1    May 27, 2021

(51) Int. Cl.
*A61B 5/1455*  (2006.01)
*G16H 40/67*  (2018.01)
(Continued)

(52) U.S. Cl.
CPC ........ *A61B 5/14551* (2013.01); *A61B 5/0022* (2013.01); *A61B 5/021* (2013.01);
(Continued)

(58) Field of Classification Search
CPC ....... A61B 5/021; A61B 5/7257; A61B 5/726; A61B 5/02156; A61B 2560/0223;
(Continued)

(56) References Cited

U.S. PATENT DOCUMENTS

| 5,725,480 A | 3/1998 | Oosta et al. |
| 8,346,327 B2 | 1/2013 | Campbell et al. |

(Continued)

FOREIGN PATENT DOCUMENTS

| CA | 2840795 C | * 10/2018 | ............. G16H 50/30 |
| CN | 101032395 A | 9/2007 | |

(Continued)

OTHER PUBLICATIONS

International Search Report in PCT/CN2017/111938 dated Apr. 28, 2018, 16 pages.
(Continued)

*Primary Examiner* — Daniel L Cerioni
*Assistant Examiner* — Jonathan E. Cooper
(74) *Attorney, Agent, or Firm* — Metis IP LLC

(57) ABSTRACT

A method implemented on a computing device having at least one processor, storage, and a communication platform connected to a network for determining blood pressure may include: receiving a request to determine blood pressure of a first subject from a terminal, obtaining data related to heart activity of the first subject, determining a personalized model for predicting blood pressure with respect to the first subject, determining the blood pressure of the first subject using the personalized model based on the data related to heart activity of the first subject, and sending the blood
(Continued)

pressure of the first subject to the terminal in response to the request.

15 Claims, 6 Drawing Sheets

(51) Int. Cl.
    *G16H 50/30*     (2018.01)
    *G16H 50/70*     (2018.01)
    *G16H 50/20*     (2018.01)
    *A61B 5/021*     (2006.01)
    *A61B 5/00*     (2006.01)
    *G16H 10/60*     (2018.01)
    *A61B 5/318*     (2021.01)
    *A61B 5/024*     (2006.01)

(52) U.S. Cl.
    CPC ........ *A61B 5/02125* (2013.01); *A61B 5/6802* (2013.01); *A61B 5/726* (2013.01); *A61B 5/7257* (2013.01); *A61B 5/7271* (2013.01); *A61B 5/7275* (2013.01); *A61B 5/7475* (2013.01); *G16H 10/60* (2018.01); *G16H 40/67* (2018.01); *G16H 50/20* (2018.01); *G16H 50/30* (2018.01); *G16H 50/70* (2018.01); *A61B 5/02416* (2013.01); *A61B 5/318* (2021.01)

(58) Field of Classification Search
    CPC .... A61B 2560/0228; A61B 2560/0238; A61B 5/1495; A61B 2017/00725; G16H 50/70
    See application file for complete search history.

(56) References Cited

U.S. PATENT DOCUMENTS

| | | | |
|---|---|---|---|
| 9,554,735 | B2 | 1/2017 | Rebec et al. |
| 2002/0169367 | A1* | 11/2002 | Bardy .................. G16H 50/20 600/300 |
| 2008/0039731 | A1 | 2/2008 | McCombie et al. |
| 2011/0004110 | A1 | 1/2011 | Shusterman |
| 2011/0054361 | A1 | 3/2011 | Sakoda et al. |
| 2012/0136261 | A1 | 5/2012 | Sethi et al. |
| 2012/0179136 | A1 | 7/2012 | Rinehart et al. |
| 2013/0012823 | A1 | 1/2013 | Ripoll et al. |
| 2013/0013327 | A1 | 1/2013 | Horseman |
| 2014/0066788 | A1 | 3/2014 | Mukkamala et al. |
| 2015/0213220 | A1 | 7/2015 | Courville |
| 2015/0313486 | A1 | 11/2015 | Mestha et al. |
| 2015/0374244 | A1 | 12/2015 | Yoo et al. |
| 2015/0377909 | A1 | 12/2015 | Cavet et al. |
| 2016/0038044 | A1* | 2/2016 | Banerjee ............ A61B 5/02007 600/480 |
| 2016/0045119 | A1 | 2/2016 | David et al. |
| 2017/0112395 | A1* | 4/2017 | Kim .................. A61B 5/02416 |
| 2017/0181649 | A1* | 6/2017 | Carter ............... A61B 5/02416 |
| 2017/0258340 | A1* | 9/2017 | Przybyszewski ...... A61B 5/725 |
| 2017/0364233 | A1 | 12/2017 | Cai |
| 2018/0116600 | A1* | 5/2018 | Basu .................. A61B 5/681 |
| 2021/0100455 | A1* | 4/2021 | Deng ................ G16H 50/20 600/300 |

FOREIGN PATENT DOCUMENTS

| | | | |
|---|---|---|---|
| CN | 101980228 A | | 2/2011 |
| CN | 102186411 A | | 9/2011 |
| CN | 102270264 A | | 12/2011 |
| CN | 102397064 A | | 4/2012 |
| CN | 102908130 A | | 2/2013 |
| CN | 102930163 A | | 2/2013 |
| CN | 103577686 A | | 2/2014 |
| CN | 103637787 A | | 3/2014 |
| CN | 104323764 A | | 2/2015 |
| CN | 104434311 A | | 3/2015 |
| CN | 104523252 A | | 4/2015 |
| CN | 104720773 A | | 6/2015 |
| CN | 204499693 U | | 7/2015 |
| CN | 105147269 A | | 12/2015 |
| CN | 105193406 A | | 12/2015 |
| CN | 105455797 A | | 4/2016 |
| CN | 105528509 A | | 4/2016 |
| CN | 105877723 A | * | 8/2016 |
| CN | 105962918 A | | 9/2016 |
| CN | 106361307 A | | 2/2017 |
| CN | 106419868 A | | 2/2017 |
| CN | 106599821 A | * | 4/2017 |
| CN | 106725376 A | | 5/2017 |
| WO | 02094085 A2 | | 11/2002 |
| WO | 2013109188 A1 | | 7/2013 |
| WO | 2014063518 A1 | | 5/2014 |
| WO | 2016155348 A1 | | 10/2016 |
| WO | 2016187847 A1 | | 12/2016 |
| WO | 2017005016 A1 | | 1/2017 |

OTHER PUBLICATIONS

Written Opinion in PCT/CN2017/111938 dated Apr. 28, 2018, 6 pages.
International Search Report in PCT/CN2017/076702 dated Jun. 7, 2017, 5 pages.
Written Opinion in PCT/CN2017/076702 dated Jun. 7, 2017, 5 pages.
First Office Action in Chinese Application No. 201780020746.0 dated Sep. 15, 2020, 19 pages.
The Extended European Search Report in European Application No. 17773043.9 dated Mar. 21, 2019, 8 pages.
International Search Report in PCT/CN2017/094762 dated May 3, 2018, 4 pages.
Written Opinion in PCT/CN2017/094762 dated May 3, 2018, 4 pages.
Zheng, Guozhong, Study on Physiological Responses of Relaive Population in Hot and Humid Environments, China Excellent Doctoral and Master's Thesis Full-text Database (Ph.D.) Medical and Health Science and Technology Series, 2015, 155 pages.
First Office Action in Chinese Application No. 201780093247.4 dated Jan. 6, 2022, 16 pages.
First Office Action in Chinese Application No. 201780093245.5 dated Dec. 17, 2021, 13 pages.

* cited by examiner

SYSTEMS AND METHODS FOR DETERMINING BLOOD PRESSURE OF A SUBJECT

This application is a U.S. national stage under 35 U.S.C. § 371 of International Application No. PCT/CN2017/094762, filed on Jul. 27, 2017, designating the United States of America, the contents of which are incorporated herein by reference in their entireties.

TECHNICAL FIELD

The present disclosure generally relates to systems and methods applicable in health-care related areas. More particularly, the present disclosure relates to systems and methods for determining blood pressure of a subject.

BACKGROUND

Blood pressure measurement can be categorized into invasive blood pressure measurement and non-invasive blood pressure measurement. Invasive blood pressure measurement is usually used in medical surgeries or medical research and needs to be conducted by the medical professionals. Non-invasive blood pressure measuring is an indirect blood pressure measuring method. A sphygmomanometer is a popular non-invasive blood pressure measuring device. It is composed of an inflatable cuff to collapse and then release the artery under the cuff in a controlled manner, and a mercury or mechanical manometer to measure the pressure. However, frequent measuring using the sphygmomanometer causes discomfort of the subject as frequent inflation oppresses the blood vessels of the subject. Further, the accuracy of the measured blood pressure is affected by the size of the cuff, elastic effects and the posture of the subject during the measurement.

Another non-invasive blood pressure measurement system uses the electrocardiosignal and the pulse wave signal to predict blood pressure of a subject. The system calculates the transmitting velocity of the pulse wave signal and determines a model for predicting the blood pressure. However, the subject needs to wear two sets of devices for measuring the electrocardiosignal and the pulse wave signal separately. Therefore, there is a need to provide a non-invasive blood pressure measurement system and method to efficiently predict the subject's blood pressure.

SUMMARY

According to one aspect of the present disclosure, a system for determining blood pressure may include at least one medium including a set of instructions, a communication platform connected to a network and at least one processor in communication with the at least one storage medium. When executing the set of instructions, the at least one processor may receive a request to determine blood pressure of a first subject from a terminal. The at least one processor may obtain data related to heart activity of the first subject in response to the request. The at least one processor may determine a personalized model for predicting blood pressure with respect to the first subject. The at least one processor may determine the blood pressure of the first subject using the personalized model based on the data related to heart activity of the first subject. The at least one processor may send the blood pressure of the first subject to the terminal in response to the request.

In some embodiments, the at least one processor may communicate with a sensor attached to the first subject. In some embodiments, the sensor may be configured to detect the heart activity of the first subject and generate a signal. The at least one processor may generate the data related to heart activity of the first subject based on the signal.

In some embodiments, the data related to the first subject includes at least one of age of the first subject, gender of the first subject, height of the first subject, weight of the first subject, posture of the first subject, time information associated with the request, whether or not the first subject has high blood pressure, and/or whether or not the first subject is under at least one medication.

In some embodiments, the at least one processor may obtain historical data related to heart activities of a plurality of second subjects. In some embodiments, the plurality of second subjects may include the first subject. In some embodiments, the historical data may include a plurality of historical blood pressure measurements with respect to the plurality of second subjects. The at least one processor may determine a preliminary model for predicting blood pressure based on the historical data related to heart activities of the plurality of second subjects. The at least one processor may generate the personalized model for predicting blood pressure with respect to the first subject based on the preliminary model for predicting blood pressure and at least part of the historical data related to heart activity of the first subject.

In some embodiments, the at least one processor may generate a first model for predicting first blood pressure based on the historical data related to heart activities of the plurality of second subjects.

In some embodiments, the at least one processor may generate a second model for predicting a plurality of residuals between the plurality of historical blood pressure measurements and values of the first blood pressure predicted by the first model based on the historical data related to heart activities of the plurality of second subjects. The at least one processor may determine the preliminary model for predicting blood pressure based on the first model, the second model, and at least part of the historical data related to heart activities of the plurality of second subjects.

In some embodiments, the at least one processor may transform the signal into a first representation in the frequency domain. The at least one processor may determine a first plurality of coefficients related to the first representation in the frequency domain. The at least one processor may generate the data related to heart activity of the first subject based on the first plurality of coefficients.

In some embodiments, the at least one processor may transform a portion of the signal into a second representation in the frequency domain. The at least one processor may determine a second plurality of coefficients related to the second representation in the frequency domain. The at least one processor may generate the data related to heart activity of the first subject based on the second plurality of coefficients.

According to another aspect of the present disclosure, a method implemented on a computing device having at least one processor, storage, and a communication platform connected to a network for determining blood pressure may include: receiving, by the at least one processor, a request to determine blood pressure of a first subject from a terminal; obtaining, by the at least one processor, data related to heart activity of the first subject in response to the request; determining, by the at least one processor, a personalized model for predicting blood pressure with respect to the first subject; determining, by the at least one processor, the blood pressure of the first subject using the personalized model based on the data related to heart activity of the first subject; and sending, by the at least one processor, the blood pressure of the first subject to the terminal in response to the request.

In some embodiments, the method may further include communicating with a sensor attached to the first subject and generating a signal and generating the data related to heart activity of the first subject based on the signal. In some embodiments, the sensor may be configured to detect the heart activity of the first subject.

In some embodiments, the method may further include obtaining historical data related to heart activities of a plurality of second subjects, determining a preliminary model for predicting blood pressure based on the historical data related to heart activities of the plurality of second subjects, and generating the personalized model for predicting blood pressure with respect to the first subject based on the preliminary model for predicting blood pressure and at least part of the historical data related to heart activity of the first subject. In some embodiments, the plurality of second subjects may include the first subject. In some embodiments, the historical data may include a plurality of historical blood pressure measurements with respect to the plurality of second subjects.

In some embodiments, the method may further include generating a first model for predicting first blood pressure based on the historical data related to heart activities of the plurality of second subjects.

In some embodiments, the method may further include generating a second model for predicting a plurality of residuals between the plurality of historical blood pressure measurements and values of the first blood pressure predicted by the first model based on the historical data related to heart activities of the plurality of second subjects and determining the preliminary model for predicting blood pressure based on the first model, the second model, and at least part of the historical data related to heart activities of the plurality of second subjects.

In some embodiments, the method may further include transforming the signal into a first representation in the frequency domain, determining a first plurality of coefficients related to the first representation in the frequency domain, and generating the data related to heart activity of the first subject based on the first plurality of coefficients.

In some embodiments, the method may further include transforming a portion of the signal into a second representation in the frequency domain, determining a second plurality of coefficients related to the second representation in the frequency domain, and generating the data related to heart activity of the first subject based on the second plurality of coefficients.

According to another aspect of the present disclosure, a system for determining blood pressure may include at least one medium including a set of instructions, a communication platform connected to a network and at least one processor in communication with the at least one storage medium. When executing the set of instructions, the at least one processor may receive a request to determine blood pressure of a first subject from a terminal. The at least one processor may obtain data related to heart activity of the first subject in response to the request. The at least one processor may obtain a personalized model for predicting blood pressure with respect to the first subject from a cloud server. The at least one processor may determine the blood pressure of the first subject using the personalized model based on the data related to heart activity of the first subject. The at least one processor may send the blood pressure of the first subject to the terminal in response to the request.

According to another aspect of the present disclosure, a system for determining blood pressure may include at least one medium including a set of instructions, a communication platform connected to a network and at least one processor in communication with the at least one storage medium. When executing the set of instructions, the at least one processor may receive a request to determine blood pressure of a first subject from a terminal. The at least one processor may obtain data related to heart activity of the first subject in response to the request. The at least one processor may send the data related to heart activity of the first subject to a cloud server. The at least one processor may receive the blood pressure of the first subject determined by the cloud server. In some embodiments, the blood pressure of the first subject may be determined by determining a personalized model for predicting blood pressure with respect to the first subject and determining the blood pressure of the first subject using the personalized model based on the data related to heart activity of the first subject. The at least one processor may send the blood pressure of the first subject to the terminal in response to the request.

According to another aspect of the present disclosure, a non-transitory computer-readable medium, comprising at least one set of instructions for determine blood pressure. When executed by at least one processor, the at least one set of instructions may direct the at least one processor to: receive a request to determine blood pressure of a first subject from a terminal; obtain data related to heart activity of the first subject in response to the request; determine a personalized model for predicting blood pressure with respect to the first subject; determine the blood pressure of the first subject using the personalized model based on the data related to heart activity of the first subject; and send the blood pressure of the first subject to the terminal in response to the request.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
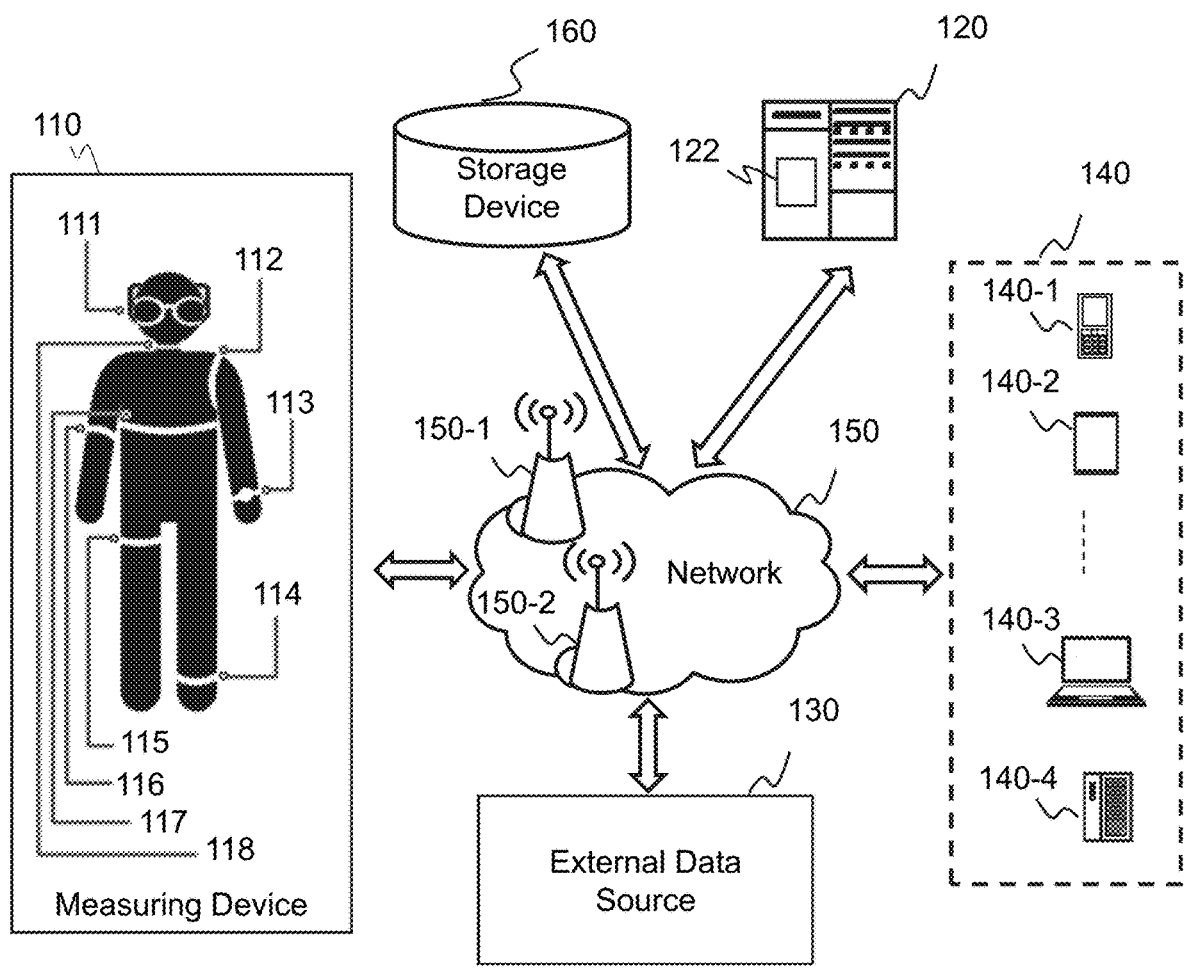
FIG. 1 illustrates an exemplary system configuration in which a medical system may be deployed in accordance with some embodiments of the present disclosure.

The following description is presented to enable any person skilled in the art to make and use the present disclosure, and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but is to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprises," "comprising," "includes," and/or "including" when used in this specification, specify the presence of stated features, integers, steps, operations, elements, and/or components, but do not preclude the presence or addition of one or more other features, integers, steps, operations, elements, components, and/or groups thereof.

These and other features, and characteristics of the present disclosure, as well as the methods of operation and functions of the related elements of structure and the combination of parts and economies of manufacture, may become more apparent upon consideration of the following description with reference to the accompanying drawing(s), all of which form a part of this specification. It is to be expressly understood, however, that the drawing(s) are for the purpose of illustration and description only and are not intended to limit the scope of the present disclosure. It is understood that the drawings are not to scale.

The flowcharts used in the present disclosure illustrate operations that systems implement according to some embodiments in the present disclosure. It is to be expressly understood, the operations of the flowchart may be implemented not in order. Conversely, the operations may be implemented in inverted order, or simultaneously. Moreover, one or more other operations may be added to the flowcharts. One or more operations may be removed from the flowcharts.

An aspect of the present disclosure relates to systems and methods for determining blood pressure of a first subject. The present disclosure provides an efficient method to predict blood pressure of the first subject based on a signal indicative heart activity of the first subject. In some embodiments, the systems and methods may obtain or determine historical data indicative of heart activities of a plurality of second subjects. The historical data may be related to a plurality of signals related to heart activities of the plurality of second subjects. The systems and methods may determine a preliminary model for predicting blood pressure based on the historical data. The systems and methods may obtain or determine data indicative of heart activity of the first subject. The data may be related to a signal indicative of heart activity of the first subject. The systems and methods may determine a personalized model for predicting blood pressure of the first subject based on the data indicative of heart activity of the first subject and the preliminary model. By using a personalized model that is trained based a plurality of historical data, the blood pressure predicting may be more efficient and the predicting accuracy may be improved.

FIG. 1 illustrates an exemplary system configuration in which a medical system 100 may be deployed in accordance with some embodiments of the present disclosure. The medical system 100 may be configured to monitor a physiological parameter of interest. The medical system 100 may include a measuring device 110, a server 120, an external data source 130, a terminal 140, and a storage device 150. Various components of the medical system 100 may be connected to each other directly or indirectly via a network 150.

The measuring device 110 may be configured to detect physiological phenomenon (e.g., heart activity) of a subject and generate a signal. The signal may be a cardiovascular signal. The signal may relate to or be used to determine a physiological parameter of interest. The measuring device 110 may include, for example, a clinical device, a household device, a portable device, a wearable device, or the like, or a combination thereof. As used herein, a clinical device may be one that meets applicable requirements and specifications to be used in a clinical setting including, e.g., a hospital, a doctor's office, a nursing home, or the like. A clinical device may be used by or with the assistance of a medical worker. As used herein, a household device may be one that meets applicable requirements and specifications to be used at home or a nonclinical setting. A household device may be used by someone who is or is not a professional provider. A clinical device or a household device, or a portion thereof, may be portable or wearable. Exemplary clinical devices include an auscultatory device, an oscillometric device, an ECG monitor, a PPG monitor, or the like, or a combination thereof. Exemplary household devices include an oscillometric device, a household ECG monitor, a sphygmometer, or the like, or a combination thereof. Exemplary portal devices include an oscillometric device, a portable ECG monitor, a portable PPG monitor, or the like, or a combination thereof. Exemplary wearable devices include a pair of glasses 111, a shoulder strap 112, a smart watch 113, an anklet 114, a thigh band 115, an armband 116, a chest belt 117, a necklet 118, or the like, or a combination thereof. The above mentioned examples of measuring devices 110 are provided for illustrative purposes, and not intended to limit the scope of the present disclosure. A measuring device 110 may be in other forms, such as a fingerstall, a wristband, a brassiere, an underwear, a chest band, a pulse oximeter, or a device associated with the principle used in a pulse oximeter, or the like, or a combination thereof.

Merely by way of example, the measuring device 110 is a wearable or portable device configured to detect and generate one or more cardiovascular signals. In some embodiments, the wearable or portable device may process at least some of the measured signals, estimate a physiological parameter of interest based on the measured signals, display a result including the physiological parameter of interest in the form of, e.g., an image, an audio alert, perform wired or wireless communication with another device or server (e.g., the server 120), or the like, or a combination thereof. In some embodiments, the wearable or portable device may communicate with another device (e.g., the terminal 140) or a server (e.g., the server 120). The device or server may process at least some of the measured signals, estimate a physiological parameter of interest based on the measured signals, display a result including the physiological parameter of interest in the form of, e.g., an image, an audio alert, or the like, or a combination thereof.

In some embodiments, the operations of processing the generated signals, estimating a physiological parameter, displaying a result, or performing wired or wireless communication may be performed by an integrated device or by separate devices connected to or communicating with each other. Such an integrated device may be portable or wearable. In some embodiments, at least some of the separate devices may be portable or wearable, or located in the vicinity of a subject from which the signal is measured or a physiological parameter of interest is estimated or monitored. Merely by way of example, the subject wears the measuring device 110 that is configured to detect and generate one or more cardiovascular signals; and the generated one or more cardiovascular signals are transmitted to a smart phone that is configured to determine a physiological parameter of interest based on the measured signals. In some embodiments, at least some of the separate devices are located in a location remote from the subject. Merely by way of example, the subject wears the measuring device 110 that is configured to detect and generate one or more cardiovascular signals; the generated one or more cardiovascular signals are further transmitted to the server 120 that is configured to determine a physiological parameter of interest based on the measured signals; and the determined physiological parameter of interest may be transmitted back to the subject, or a user other than the subject (e.g., a doctor, a care provider, a family member relating to the subject, or the like, or a combination thereof).

In some embodiments, the measuring devices 110 may incorporate various types of sensors, e.g., an electrode sensor, an optical sensor, a photoelectric sensor, a pressure sensor, an accelerometer, a gravity sensor, a temperature sensor, a moisture sensor, or the like, or a combination thereof. The measuring device 110 may be configured to monitor and/or detect one or more types of variables including, for example, temperature, humidity, user or subject input, or the like, or a combination thereof. The gravity sensor may detect the posture of the measured subject. The posture may include lying, sitting, standing, etc. The temperature sensor may detect the temperature of a position near the measuring device 110. The moisture sensor may detect the humidity of an area near the measuring device 110. The measuring devices 110 may also incorporate a positioning system, e.g., a GPS receiver, or a location sensor, and the position information may be transmitted to the server 120, the external data source 130, the terminal 140, or the like, or a combination thereof, through the network 150. The position information and measured signals may be transmitted simultaneously or successively. In some embodiments, the measuring device 110 may incorporate one or more computer chips on which the functions of the server 120 as described below may be implemented.

The server 120 may be a cloud server. Merely by way of example, the server 120 may be implemented in a cloud server that may provide storage capacity, computation capacity, or the like, or a combination thereof. The server may include a storage device configured to collect or store data. The data may include personal data, non-personal data, or both. The data may include static data, dynamic data, or both. Exemplary static data may include various information regarding a subject including identity, contact information, birthday, a health history (e.g., whether a subject has a history of smoking, information regarding a prior surgery, a food allergy, a drug allergy, a medical treatment history, a history of genetic disease, a family health history, or the like, or a combination thereof), the gender, the nationality, the height, the weight, the occupation, a habit (e.g., a health-related habit such as an exercise habit), the education background, a hobby, the marital status, religious belief, or the like, or a combination thereof. Exemplary dynamic data may include a current health condition of a subject, medications the subject is taking, a medical treatment the subject is undertaking, diet, physiological signals or parameters (e.g., pulse transit time (PTT), systolic blood pressure (SBP), diastolic blood pressure (DBP), or the like) relating to the subject for multiple time points or over a period of time, or the like, or a combination thereof.

As used herein, a subject may refer to a person or animal whose signal or information is acquired and whose physiological parameter is determined or monitored. Merely by way of example, a subject may be a patient whose cardiovascular signals are acquired, and blood pressure determined or monitored based on the acquired cardiovascular signals.

In some embodiments, the server 120 may be a single server, or a server group. The server group may be centralized, or distributed (e.g., server 110 may be a distributed system). In some embodiments, the server 120 may be local or remote. For example, the server 120 may access information and/or data stored in the terminal 140 and/or the storage device 150 via the network 150. As another example, the server 120 may connect the terminal 140 and/or the storage device 150 to access stored information and/or data. In some embodiments, the server 120 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the server 120 may be implemented on a computing device 200 having one or more components illustrated in FIG. 2 in the present disclosure.

In some embodiments, the server 120 may include a processing engine 122. The processing engine 122 may process information and/or data to perform one or more functions described in the present disclosure. For example, the processing engine 122 may determine blood pressure of a subject based on one or more personalized models, data related to the generated signals, and/or information related to the subject. In some embodiments, the processing engine 122 may include one or more processing engines (e.g., single-core processing engine(s) or multi-core processor(s)). Merely by way of example, the processing engine 122 may include one or more hardware processors, such as a central processing unit (CPU), an application-specific integrated circuit (ASIC), an application-specific instruction-set processor (ASIP), a graphics processing unit (GPU), a physics processing unit (PPU), a digital signal processor (DSP), a field programmable gate array (FPGA), a programmable logic device (PLD), a controller, a microcontroller unit, a reduced instruction-set computer (RISC), a microprocessor, or the like, or any combination thereof.

The external data sources 130 may include a variety of organizations, systems, and devices, or the like, or a combination thereof. Exemplary data sources 130 may include a medical institution, a research facility, a conventional device, and a peripheral device, or the like, or a combination thereof. The medical institution or the research facility may provide, for example, personal medical records, clinical test results, experimental research results, theoretical or mathematical research results, algorithms suitable for processing data, or the like, or a combination thereof. The conventional device may include a cardiovascular signal measuring device, such as a mercury sphygmomanometer. A peripheral device may be configured to monitor and/or detect one or more types of variables including, for example, temperature, humidity, user or subject input, or the like, or a combination thereof. The above mentioned examples of the external data sources 130 and data types are provided for illustration purposes, and not intended to limit the scope of the present disclosure. For instance, the external data sources 130 may include other sources and other types of data, such as genetic information relating to a subject or his family.

The terminal 140 in the medical system 100 may be configured for processing at least some of the generated signals, determining a physiological parameter of interest based on the generated cardiovascular signals, displaying a result including the physiological parameter of interest in the form of, e.g., an image, storing data, controlling access to the medical system 100 or a portion thereof (e.g., access to the personal data stored in the medical system 100 or accessible from the medical system 100), managing input-output from or relating to a subject, or the like, or a combination thereof.

The terminal 140 may include a mobile device 130-1, a tablet computer 140-2, a laptop computer 140-3, a built-in device in a motor vehicle 140-4, or the like, or any combination thereof. In some embodiments, the mobile device 140-1 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a smart bracelet, a smart footgear, a smart glass, a smart helmet, a smart watch, a smart clothing, a smart backpack, a smart accessory, or the like, or any combination thereof. In some embodiments, the smart mobile device may include a smartphone, a personal digital assistance (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google Glass™, a RiftCon™, a Fragments™, a Gear VR™, etc. In some embodiments, built-in device in the motor vehicle 140-4 may include an onboard computer, an onboard television, etc.

The network 150 may facilitate exchange of information and/or data. In some embodiments, one or more components of the medical system 100 (e.g., the measuring device 110, the server 120, the external data source 130, the terminal 140, and the storage device 160) may transmit information and/or data to other component(s) in the medical system 100 via the network 150. For example, the server 120 may receive a request for determining blood pressure of a subject from the terminal 140 via the network 150. In some embodiments, the network 150 may be any type of wired or wireless network, or combination thereof. Merely by way of example, the network 150 may include a cable network, a wireline network, an optical fiber network, a tele communications network, an intranet, an Internet, a local area network (LAN), a wide area network (WAN), a wireless local area network (WLAN), a metropolitan area network (MAN), a wide area network (WAN), a public telephone switched network (PSTN), a Bluetooth network, a ZigBee network, a near field communication (NFC) network, or the like, or any combination thereof. In some embodiments, the network 150 may include one or more network access points. For example, the network 150 may include wired or wireless network access points such as base stations and/or internet exchange points 150-1, 150-2, . . . , through which one or more components of the medical system 100 may be connected to the network 150 to exchange data and/or information between them.

The storage device 160 may store data and/or instructions. In some embodiments, the storage device 160 may store data obtained from the terminal 140. In some embodiments, the storage device 160 may store data and/or instructions that the server 120 may execute or use to perform exemplary methods described in the present disclosure. In some embodiments, the storage device 160 may include a mass storage, a removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 160 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 160 may be connected to the network 150 to communicate with one or more components of the medical system 100 (e.g., the measuring device 110, the server 120, the external data source 130, the terminal 140, and the storage device 160). One or more components in the medical system 100 may access the data or instructions stored in the storage device 160 via the network 150. In some embodiments, the storage device 160 may be directly connected to or communicate with one or more components in the medical system 100 (e.g., the measuring device 110, the server 120, the external data source 130, the terminal 140, and the storage device 160).

In some embodiments, one or more components of the service medical system 100 (e.g., the measuring device 110, the server 120, the external data source 130, the terminal 140, and the storage device 160) may access the storage device 160. For example, the server 110 may read and/or modify one or more users' information after a request for predicting blood pressure of a subject.

In some embodiments, various components of the medical system 100 may include a storage device for storing intermediate data and/or information. Such components may include, for example, the measuring device 110, the server 120, the external data sources 130, the terminal 140, or the like, or a combination thereof.

In some embodiments, the external data source 130 may receive data from the measuring device 110, the sever 120, the terminal 140, or the like, or any combination via the network 150. Merely by way of example, the external data source 130 (e.g., a medical institution, or a smart home system, or the like) may receive information related to a subject (e.g., location information, data from the cloud sever or a terminal, or the like, or a combination thereof) based on the data received from the measuring devices 110 or the terminals 140. In some other embodiments, the measuring device 110 may receive data from the sever 120, the external data source 130, or the like, or any combination, via the network 150. Merely by way of example, the measuring device 110 may receive the information related to a subject (e.g., a current/historical health condition of a subject, medications the subject is taking, medical treatment the subject is undertaking, current/historical diets, current emotion status, historical physiological parameters (e.g., PTT, SBP, DBP) relating to the subject, or the like, or a combination thereof). Furthermore, the terminal 140 may receive data from the measuring device 110, the server 120, the external data source 130, or the like, or a combination thereof. In some embodiments, the server 120 may store one or more personalized models for predicting blood pressure and may transmit the personalized models to the measuring device 110 and the terminal 140.

FIG. 1 is a specific example of the medical system 100, and the configuration of the medical system 100 is not intended to limit the scope of the present disclosure. For example, a server 120 may be omitted, migrating all of its functions to the terminal 140. In another example, the server 120 and the terminal 140 may both be omitted, migrating all of their functions to a measuring device 110. The system may include various devices or combinations of devices in different embodiments.

Figure 2:
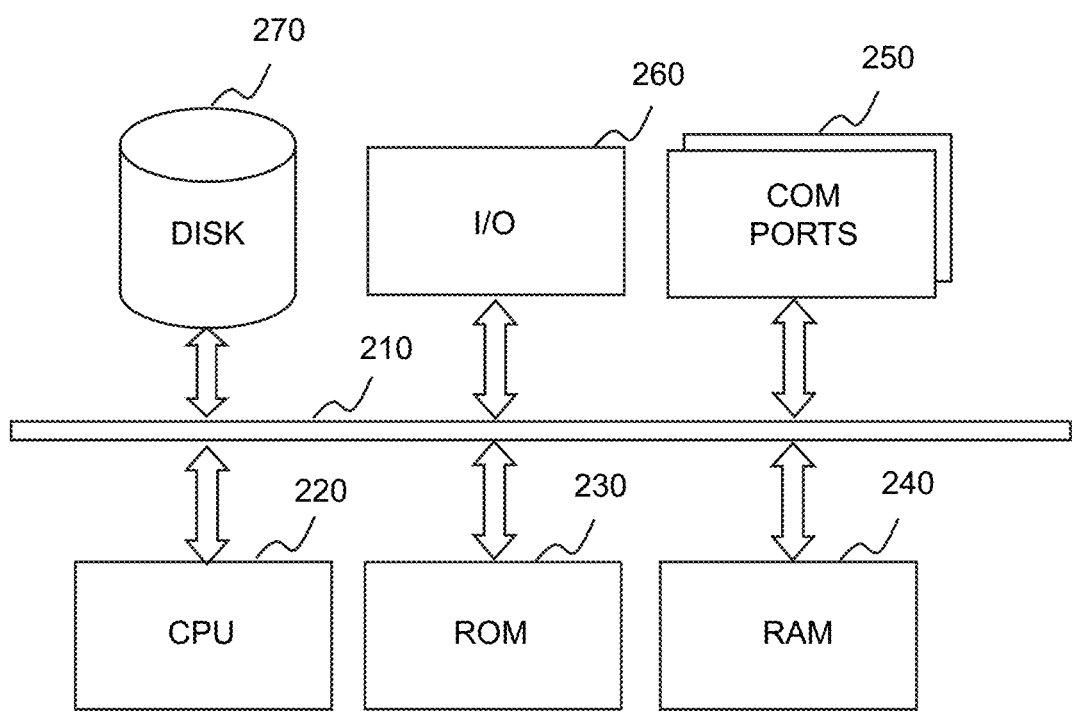
FIG. 2 is a schematic diagram illustrating exemplary hardware and software components of a computing device according to some embodiments of the present disclosure.

FIG. 2 is a schematic diagram illustrating exemplary hardware and software components of a computing device 200 on the measuring device 110, the server 120, the external data source 130, the terminal 140, and the storage device 160 may be implemented according to some embodiments of the present disclosure. For example, the processing engine 122 may be implemented on the computing device 200 and configured to perform functions of the processing engine 122 disclosed in this disclosure.

The computing device 200 may be a general-purpose computer or a special purpose computer; both may be used to implement a system for the present disclosure. The computing device 200 may be used to implement any component of the as described herein. For example, the processing engine 122 may be implemented on the computing device 200, via its hardware, software program, firmware, or a combination thereof. Although only one such computer is shown, for convenience, the computer functions relating to the medical system 100 as described herein may be implemented in a distributed fashion on a number of similar platforms, to distribute the processing load.

The computing device 200, for example, may include COM ports 250 connected to and from a network connected thereto to facilitate data communications. The computing device 200 may also include a processor (e.g., the CPU 220), in the form of one or more processors, for executing program instructions. The exemplary computing device may include an internal communication bus 210, program storage and data storage of different forms including, for example, a disk 270, and a read only memory (ROM) 230, or a random access memory (RAM) 240, for various data files to be processed and/or transmitted by the computing device. The exemplary computing device may also include program instructions stored in the ROM 230, RAM 240, and/or other type of non-transitory storage medium to be executed by the CPU 220. The methods and/or processes of the present disclosure may be implemented as the program instructions. The computing device 200 also includes an I/O component 260, supporting input/output between the computer and other components. The computing device 200 may also receive programming and data via network communications.

Merely for illustration, only one CPU and/or processor is illustrated in FIG. 2. Multiple CPUs and/or processors are also contemplated; thus operations and/or method steps performed by one CPU and/or processor as described in the present disclosure may also be jointly or separately performed by the multiple CPUs and/or processors. For example, if in the present disclosure the CPU and/or processor of the computing device 200 executes both step A and step B, it should be understood that step A and step B may also be performed by two different CPUs and/or processors jointly or separately in the computing device 200 (e.g., the first processor executes step A and the second processor executes step B, or the first and second processors jointly execute steps A and B).

Figure 3:
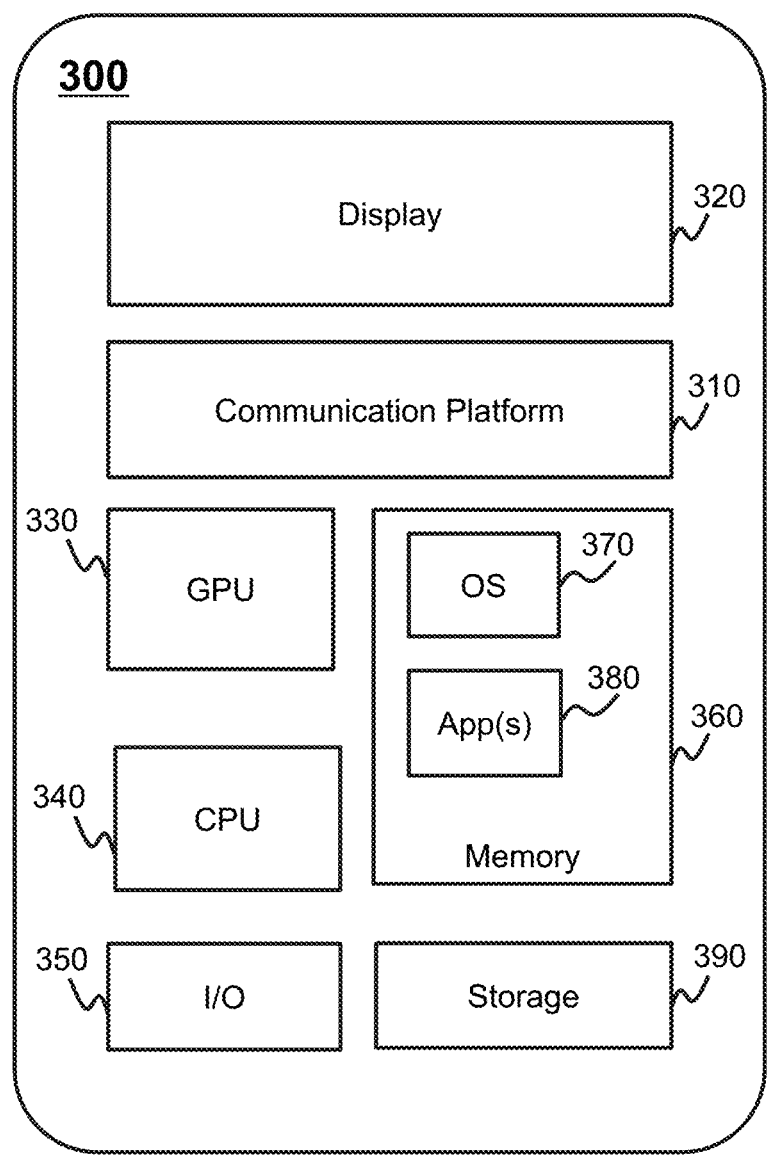
FIG. 3 is a schematic diagram illustrating exemplary hardware and/or software components of an exemplary mobile device on which a use terminal may be implemented according to some embodiments of the present disclosure.

FIG. 3 is a schematic diagram illustrating exemplary hardware and/or software components of an exemplary mobile device 300 on which a use terminal may be implemented according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing engine 122. User interactions with the information stream may be achieved via the I/O 350 and provided to the processing engine 122 and/or other components of the medical system 100 via the network 150.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
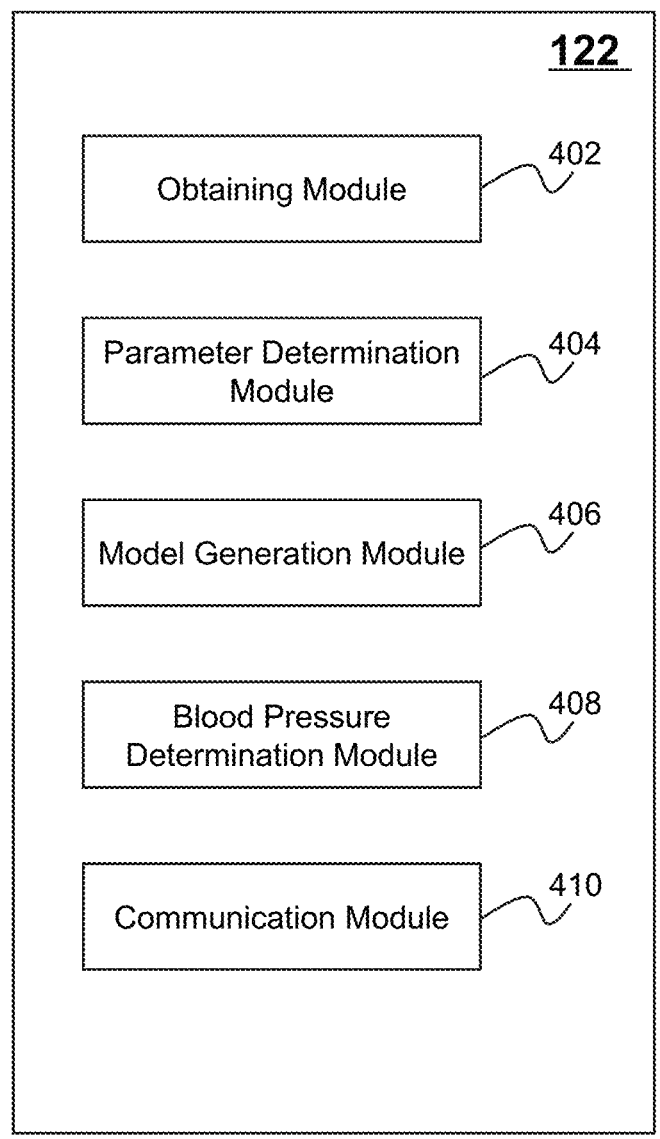
FIG. 4 is a block diagram illustrating an exemplary processing engine according to some embodiments of the present disclosure.

FIG. 4 is a block diagram illustrating an exemplary processing engine 122 according to some embodiments of the present disclosure. The processing engine 122 may include an obtaining module 402, a parameter determination module 404, a model generation module 406, a blood pressure determination module 408 and a communication module 410. Each module may be a hardware circuit that is designed to perform the following actions, a set of instructions stored in one or more storage media, and/or any combination of the hardware circuit and the one or more storage media.

The obtaining module 402 may be configured to obtain a signal indicative of heart activity of a first subject. The signal may be physiological signals including but not limited to an electrocardiogram (ECG) signal, a pulse-wave-related signal (e.g., photoplethysmogram (PPG)), a phonocardiogram (PCG) signal, an impedance cardiogram (ICG) signal, or the like, or any combination thereof. The obtaining module 402 may also obtain information related to the first subject. The information may include vital information associated with the first subject.

The parameter determination module 404 may be configured to determine data based on the signal obtained by the obtaining module 402. In some embodiments, the parameter determination module 404 may determine the data based on a characteristic point of a beat of the signal. In some embodiments, the parameter determination module 404 may transform the signal from the time domain to the frequency domain and determine a representation of the signal in the frequency domain. The parameter determination module 404 may determine the data based on the representation.

The model generation module 406 may be configured to determine a personalized model for predicting blood pressure with respect to the first subject. The model generation module 406 may obtain historical data indicative of heart activities related to a plurality of second subjects. The model generation module 406 may also obtain historical information related to the plurality of second subjects.

The plurality of second subjects may include the first subject. The model generation module 406 may determine a preliminary model for predicting blood pressure based on the historical data and the historical information. The model generation module 406 may determine the personalized model for predicting blood pressure based on the historical data, the historical information, and the preliminary model.

The blood pressure determination module 408 may be configured to determine the blood pressure of the first subject. The blood pressure determination module 408 may determine the blood pressure of the first subject using the personalized model based on the data indicative of heart activity of the first subject and the information related to the first subject.

The communication module 410 may be configured to send the blood pressure of the first subject to the terminal 130. The terminal 140 may correspond to the first subject. The second blood pressure may be displayed on the terminal 140 by presenting a user interface (not shown).

The modules in the processing engine 122 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. In some embodiments, any two of the modules may be combined as a single module, and any one of the modules may be divided into two or more units.

Figure 5:
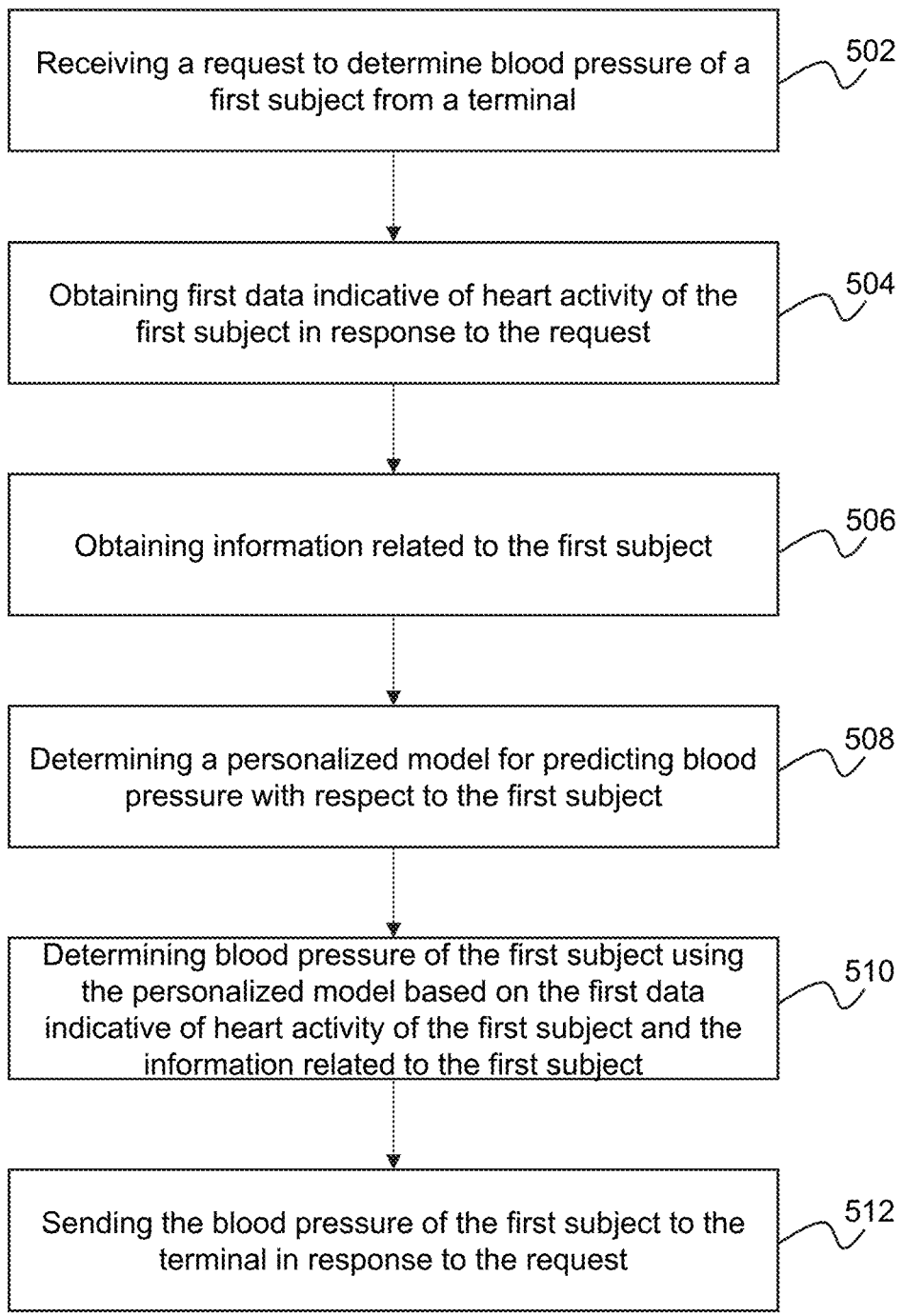
FIG. 5 is a flow chart illustrating a process and/or method for providing blood pressure of a first subject to a terminal in response to a request according to some embodiments of the present disclosure.

FIG. 5 is a flow chart illustrating a process and/or method 500 for providing blood pressure of a first subject to a terminal in response to a request according to some embodiments of the present disclosure. The process and/or method 500 may be executed by the medical system 100. For example, the process and/or method 500 may be implemented as a set of instructions (e.g., an application) stored in the storage ROM 230 or RAM 240. The CPU 210 may execute the set of instructions and may accordingly be directed to perform the process and/or method 500. The operations of the illustrated process/method presented below are intended to be illustrative. In some embodiments, the process/method may be accomplished with one or more additional operations not described, and/or without one or more of the operations discussed. Additionally, the order in which the operations of the process/method as illustrated in FIG. 5 and described below is not intended to be limiting.

In step 502, the processing engine 122 may receive a request to determine blood pressure of a first subject from the terminal 140. In some embodiments, the user may initiate and send the request by the terminal. In some embodiments, a person other than the user (e.g., a medical worker) may initiate and send the request by the terminal.

In step 504, the obtaining module 402 may obtain or determine first data indicative of heart activity of the first subject in response to the request. The first data may be related to a signal indicative of heart activity. Merely by way of example, the signal may be physiological signals including but not limited to an electrocardiogram (ECG) signal, a pulse-wave-related signal (e.g., photoplethysmogram (PPG)), a phonocardiogram (PCG) signal, an impedance cardiogram (ICG) signal, or the like, or any combination thereof. In some embodiments, the first data may be related to a pulse-wave-related signal (e.g., photoplethysmogram (PPG)).

The measuring device 110 may be attached to the first subject and detect the heart activity of the first subject. The measuring device 110 may generate the signal indicative heart activity by the detecting. The measuring device 110 (or other sensors) may also detect the temperature and/or humidity of an area near the measuring device 110.

The signal may be stable for a predetermined time period. The predetermined time period may be default settings of the medical system 100 or adjusted in different conditions. The predetermined time period may be any time span (e.g., 10 seconds, 15 seconds, 20 seconds, 30 seconds, etc.). A wave form representing the signal may be displayed on a user interface (not shown) of a terminal (e.g., the terminal 140). An exemplary wave form representing the signal is illustrated in FIG. 7, where the coordinate system associated with the wave form may include a lateral axis (i.e., x axis) denoting time and a vertical axis (i.e., y axis) denoting amplitude. The amplitude may indicate a blood volume in a vessel of the first subject generated by the measuring device 110 attached to the first subject. The signal within the predetermined time period may include a plurality of beats. A beat may correspond to a period of the signal.

In some embodiments, the parameter determination module 404 may determine the first data based on the signal. For each beat of the signal, the parameter determination module 404 may determine a characteristic point (e.g., wave crest, trough of the wave, etc.). The parameter determination module 404 may determine a time value, an amplitude value, an area value, a derivative related to the characteristic point, etc. The time value and the amplitude value may be the abscissa and the ordinate of the characteristic point, respectively. The area value may be an integral between a time interval [a, b] as will be descried in detail in connection with FIG. 7. The area value may indicate the change of the blood volume in a vessel close to the attached measuring device 110. The derivative may include a first derivative, a second derivative, a third derivative, a higher derivative, or the like, or a combination thereof. For the plurality of beats, the processing engine 122 may determine a plurality of time values, a plurality of amplitude values, a plurality of area values, a plurality of derivatives, etc.

In some embodiments, the parameter determination module 404 may determine second data based on the plurality of time values, the plurality of amplitude values, the plurality of area values, and/or the plurality of derivatives. For example, the second data may be a variance, a standard deviation, an interquartile range, an average value, a median value, and/or a weighted value of the plurality of time values. As another example, the second data may be a variance, a standard deviation, an interquartile range, an average value, a median value, and/or a weighted value of the plurality of amplitude values. As another example, the second data may be a variance, a standard deviation, an interquartile range, an average value, a median value, and/or a weighted value of the plurality of area values. As yet another example, the second data may be a variance, a standard deviation, an interquartile range, an average value, a median value, and/or a weighted value of the plurality of derivatives.

In some embodiments, the parameter determination module 404 may determine third data related to the signal by transforming the signal from the time domain to the frequency domain. The parameter determination module 404 may determine a representation related to the signal in the frequency domain. The time-frequency transformation may include but is not limited to the Fourier transform, the wavelet transform, the Laplace transform, the Z-transform, the like, or any combination thereof. The Fourier transform may include, but is not limited to, Prime-factor FFT algorithm, Bruun's FFT algorithm, Rader's FFT algorithm, Bluestein's FFT algorithm, etc.

In some embodiments, the parameter determination module 404 may use the Fourier transform to transform the signal from the time domain to the frequency domain and then determine a first representation in the frequency domain. The parameter determination module 404 may determine the third data based on the first representation. For example, the first representation may be expressed by Equation (1):

$$f(x) = \frac{a_0}{2} + \sum_{l=1}^{\infty}[a_l \cdot \cos(l \cdot x) + b_l \cdot \sin(l \cdot x)]. \quad (1)$$

where $a_l$ (l=0, 1, 2, ..., ∞) and $b_l$ (l=1, 2, ..., ∞) may refer to coefficients associated with cos(l·x) and sin(l·x), respectively. The parameter determination module 404 may determine the third data based on the coefficients of Equation (1). For example, the third data may include $a_l$ (l=0, 1, 2, ..., ∞) and/or $b_l$ (l=1, 2, ..., ∞).

In some embodiments, the parameter determination module 404 may use the wavelet transform to transform a portion of the signal from the time domain to the frequency domain and then determine a second representation in the frequency domain. The portion of the signal may include at least one beat of the signal. The parameter determination module 404 may determine the third data based on the second representation. For example, the second representation may be expressed by Equation (2):

$$X(g, h) = \frac{1}{h} \cdot \int_{-\infty}^{\infty} x(t) \cdot \Psi\left(\frac{t-g}{h}\right) \cdot dt \quad (2)$$

where X(g, h) may refer to the portion of the signal in the frequency domain, h may refer to the scale factor, g may refer to the central position of the portion of the signal. The processing engine 122 may determine the third data based on the coefficients of Equation (2). For example, the third data may be associated with m and/or n.

It should be noted that Equation (1) and Equation (2) are for illustrative and the present disclosure is not intended to be limiting. The representation in frequency domain may have other forms. Accordingly, the third data may be in other forms.

The parameter determination module 404 may determine the first data based on the second data and/or the third data. For example, the first data may include the second data and the third data. The first data may further include but not limited to the temperature, the humidity, or the like, or a combination thereof. In some embodiments, the measuring device 110 may process the signal and determine the first data. The first signal may be stored in the measuring device 110 and/or the storage device 160.

In step 506, the obtaining module 402 may obtain information related to the first subject. The information may include vital information associated with the first subject. The vital information may include but not limited to gender of the first subject, age of the subject, height of the first subject, weight of the first subject, posture of the first subject at a time when the signal is obtained, the time when the signal is obtained, whether or not the first subject is with high blood pressure, whether or not the first subject is under at least one medication, names and birthdays of family members, addresses and phone numbers of family members' homes, emergency contact information, list of current medications and doses, list of allergies, list of any medical devices (e.g., pacemakers), list of current doctors and office phone numbers, insurance card copies, DNR (do not resuscitate) orders and form, Power of Attorney (POA) forms, or the like, or a combination thereof. The posture of the first subject at the time when the signal is obtained may include lying, sitting, standing, etc. The medication may influence blood pressure of the first subject. The information may be input to the terminal 140. The obtaining module 404 may obtain the information from the terminal 140 via the network 150. In some embodiments, the terminal 140 may store part of the information (e.g., the time when the signal is obtained) and automatically generate the information. The information may be stored in the terminal 140 and/or the storage device 160. In some embodiments, the obtaining module 402 may the information from the external data source 130.

In step 508, the model generation module 406 may determine a personalized model for predicting blood pressure with respect to the first subject. The model generation module 406 may obtain historical data indicative of heart activities related to a plurality of second subjects. The model generation module 406 may also obtain historical information related to the plurality of second subjects. The plurality of second subjects may include the first subject.

In some embodiments, the model generation module 406 may determine a preliminary first model for predicting first blood pressure based on the historical data and the historical information. The model generation module 406 may determine a plurality of sub-models based on the historical data and the historical information. The model generation module 406 may determine a preliminary second model based on the preliminary first model and the historical data and the historical information. The preliminary second model may predict a residual between a historical blood pressure measurement and the first predicted blood pressure associated with one of the plurality of second subjects. The model generation module 406 may determine a preliminary model for predicting blood pressure related to the plurality of second subjects based on the preliminary first model, the plurality of sub-models, the preliminary second model, and at least part of the historical information.

In some embodiments, for each second subject, the model generation module 406 may determine a personalized model for predicting blood pressure related to the each second subject based on the preliminary first model, the plurality of sub-models, the preliminary second model, the historical data corresponding to the each second subject, and the historical information corresponding to the each second subject. For each second subject, the model generation module 406 may determine a personalized first model for predicting first blood pressure based on the preliminary first model, the historical data corresponding to the each second subject, and the historical information corresponding to the each second subject. For each second subject, the model generation module 406 may determine a plurality of personalized sub-models based on the plurality of sub-models, the historical data corresponding to the each second subject, and the historical information corresponding to the each second subject. For each second subject, the model generation module 406 may determine a personalized second model based on the preliminary second model, the historical data corresponding to the each second subject, and the historical information corresponding to the each second subject. The model generation module 406 may determine the personalized model based on the personalized first model, the plurality of personalized sub-models, the personalized second model, and at least part of the historical information associated with the each second subject. For example, the model generation module 406 may determine a personalized first model, a personalized second model, a plurality of personalized sub-models, and a personalized model for predicting blood pressure with respect to the first subject. Detailed description of determining the personalized model for predicting blood pressure will be described in FIG. 6. The personalized first model, the personalized second model, and the personalized model may be stored in the server 120 (e.g., a cloud server) and/or the storage device 160.

In step 510, the blood pressure determination module 408 may determine the blood pressure of the first subject using the personalized model based on the first data indicative of heart activity of the first subject and the information related to the first subject. The blood pressure determination module 408 may determine first blood pressure with respect to the first subject based on the personalized first model. The blood pressure determination module 408 may determine a plurality of blood pressure values based on the plurality of personalized sub-models. The blood pressure determination module 408 may determine a residual associated with the predicted first blood pressure with respect to the first subject. The blood pressure determination module 408 may determine second blood pressure using the personalized model based on the first blood pressure with respect to the first subject, the plurality of blood pressure values, and the residual associated with the first blood pressure.

The medical system 100 may adopt various methods to determine the second blood pressure. In some embodiments, the measurement device 110 may generate and store the first data indicative of heart activity of the first subject. The terminal 140 (e.g., an application) may obtain and store the information related to the first subject. The personalized first model, the personalized second model, and the personalized model may be stored in the server 120 (e.g., a cloud server).

In some embodiments, the terminal 140 (e.g., an application) may obtain the personalized first model, the personalized second model, and the personalized model from the server 120 (e.g., a cloud server). The terminal 140 may transmit the information related to the first subject, the personalized first model, the personalized second model, and the personalized model to the measurement device 110. The measurement device 110 may generate first data indicative of heart activity of the first subject. The measurement device 110 may determine the second blood pressure using the personalized first model, the personalized second model, and the personalized model based on the first data and the information related to the first subject. In some embodiments, the measuring device 110 may determine the personalized model via one or more computer chips incorporated therein. Detailed description may be described in connection with step 612.

In some embodiments, the measurement device 110 may transmit first data indicative of heart activity of the first subject to the terminal 140 (e.g., an application). The terminal 140 may also obtain the personalized first model, the personalized second model, and the personalized model from the server 120. The terminal 140 may determine the second blood pressure using the personalized first model, the personalized second model, and the personalized model based on the first data and the information related to the first subject.

In another embodiment, the terminal 140 (e.g., an application) may obtain first data indicative of heart activity of the first subject generated by the measurement device 110. The terminal 140 may transmit the first data and the information related to the first subject to the server 120. The server 120 (e.g. the processing engine 122) may determine the second blood pressure using the personalized first model, the personalized second model, and the personalized model based on the first data and the information related to the first subject.

In step 512, the communication module 410 may send the second blood pressure of the first subject to the terminal 140 in response to the request. The terminal 140 may correspond to the first subject. The second blood pressure may be displayed on the terminal 140 by presenting a user interface (not shown).

It should be noted the methods for providing the second blood pressure related to the first subject is for illustrative but not intended to limit the scope of the present disclosure. For persons having ordinary skills in the art, it is obvious to use other methods to determine the second blood pressure related to the first subject. However, those methods may not depart from the spirit and scope of this disclosure.

Figure 6:
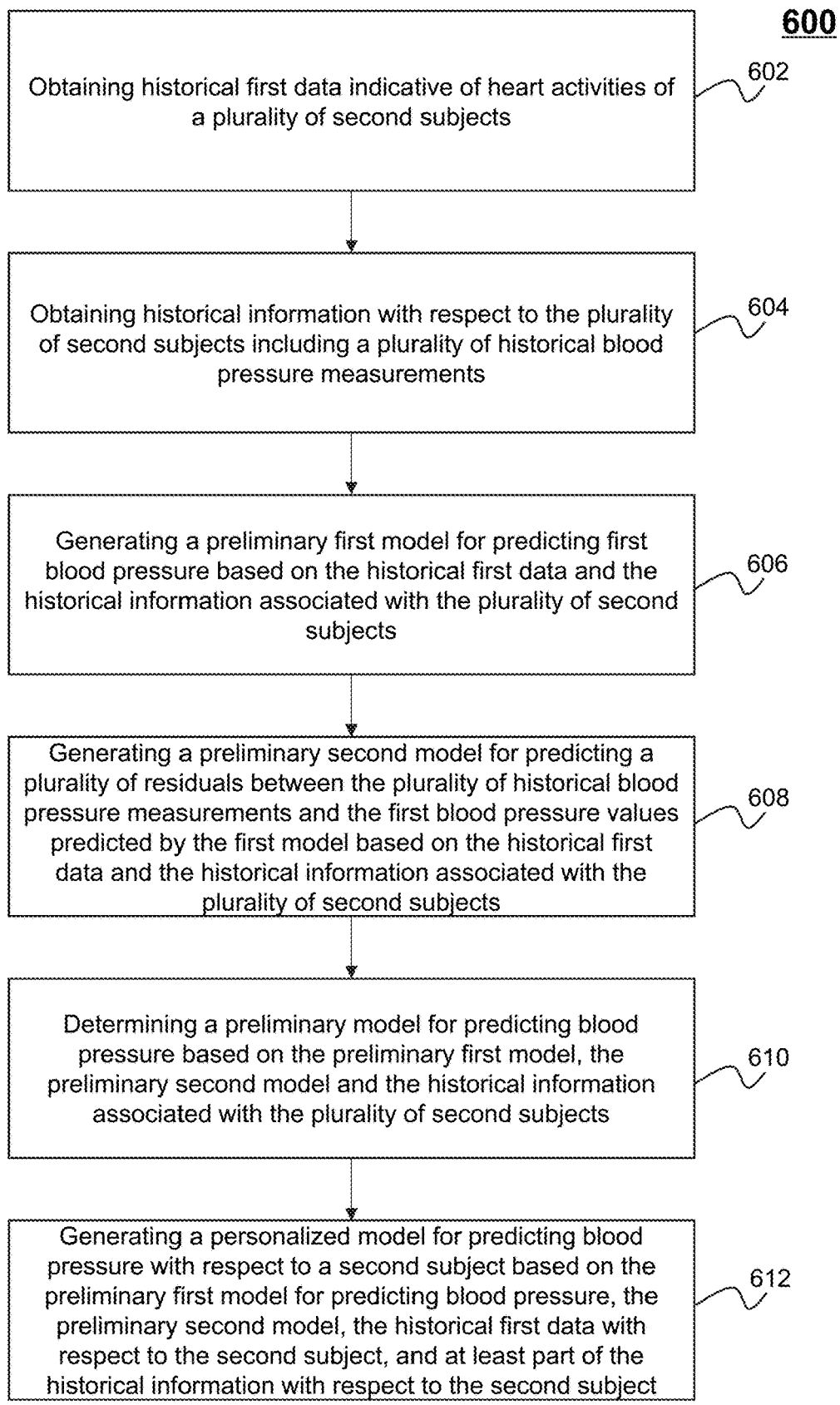
FIG. 6 is a flow chart illustrating a process and/or method for generating a personalized model for predicting blood pressure with respect to the first subject according to some embodiments of the present disclosure.

FIG. 6 is a flow chart illustrating a process and/or method 600 for generating a personalized model for predicting blood pressure with respect to the first subject according to some embodiments of the present disclosure. The process and/or method 600 may be executed by the medical system 100. For example, the process and/or method 500 may be implemented as a set of instructions (e.g., an application) stored in the storage ROM 230 or RAM 240. The CPU 210 may execute the set of instructions and may accordingly be directed to perform the process and/or method 600. The operations of the illustrated process/method presented below are intended to be illustrative. In some embodiments, the process/method may be accomplished with one or more additional operations not described, and/or without one or more of the operations discussed. Additionally, the order in which the operations of the process/method as illustrated in FIG. 6 and described below is not intended to be limiting.

In step 602, the model generation module 406 may obtain historical first data indicative of heart activities of a plurality of second subjects. As described in connection with step 504, the term "historical first data" may refer to first data indicative of heart activities of a plurality of second subjects acquired at any time (e.g., several months ago, several days ago, several hours ago, several minutes ago, etc.). The medical system 100 may save this first data as historical first data into a storage component (e.g., the storage device 160, a storage unit in the measuring device 110). In some embodiments, the plurality of second subjects may include the first subject.

The model generation module 406 may determine the historical first data based on a plurality of historical signals indicative of heart activities of the plurality of second subjects. The measuring device 110 may detect physiological phenomenon (e.g., heart activities) and generate the plurality of historical signals at any time (e.g., several months ago, several days ago, several hours ago, several minutes ago, etc.). As described in connection with step 504, the historical first data may include historical second data and historical third data. The historical second data may be related to a plurality of time values, a plurality of amplitude values, and/or a plurality of area values associated with the plurality of historical signals indicative of heart activities of the plurality of second subjects. The historical third data may be associated with coefficients of a plurality of representations of the plurality of historical signals in the frequency domain. The historical first data may further include but not limited to historical temperature, historical humidity, or the like, or a combination thereof.

In step 604, the model generation module 406 may obtain historical information with respect to the plurality of second subjects. As described in connection with step 506, the term "historical information" may refer to information related to the plurality of second subjects acquired at any time (e.g., several months ago, several days ago, several hours ago, several minutes ago, etc.). The medical system 100 may save the information as historical information into a storage component (e.g., the storage device 160, a storage unit in the terminal 140).

Compared with the information in step 506, the historical information used herein may further include a plurality of historical blood pressure measurements related to the plurality of second subjects. In some embodiments, the historical blood pressure measurements may be measured by a sphygmomanometer (e.g., an aneroid sphygmomanometer, a mercurial sphygmomanometer, an automatic sphygmomanometer, an electronic sphygmomanometer, etc.). For each second subject, a plurality of historical blood pressure measurements may be collected. The plurality of historical blood pressure measurements related to each second subject may be collected with respect to one or more postures of the each second subject when the blood pressure was measured. The posture may including lying, sitting, standing, etc. In some embodiments, the plurality of historical blood pressure measurements related to each second subject may be collected with respect to the time during a day. For example, the plurality of historical blood pressure measurements may be continuously collected at 9 am everyday for three months. In some embodiments, the plurality of historical blood pressure measurements related to each second subject may be collected with respect to the age. For example, the plurality of historical blood pressure measurements may be continuously collected at the annual check-up from 40 to 45 years old. In some embodiments, the obtaining module 402 may obtain the historical information from the external data source 130.

In some embodiments, the model generation module 406 may combine the historical first data as described in connection with step 602 and the historical information as described in connection with step 604 as sample data. The sample data may correspond to a first predetermined times of measurements for each second subject. The first predetermined times of measurements may include the first three measurements, the first five measurements, the first ten measurements, etc. In some embodiments, the model generation module 406 may similarly determine calibration sample data. The calibration sample data may correspond to a second predetermined times of measurements for each second subject. The second determined times of measurements may include the second three measurements, the second five measurements, the second ten measurements, etc. In some embodiments, the sample data may include the calibration sample data. In some embodiments, the sample data and the calibration sample data may or may not overlap. The sample data and the calibration sample data may each include a plurality of sets of data. Each of the plurality of sets of data may include historical first data and historical information associated with the each second subject corresponding to at least one measurement.

In some embodiments, for each second subject, the historical signal may be obtained for a plurality of times (e.g., 3 times, 5 times, 10 times, etc.). At each of the plurality of times, the model generation module 406 may determine a set of data including corresponding historical first data and corresponding historical information. For example, after obtaining the historical blood pressure measurement associated with a second subject from the historical signal, the model generation module 406 may determine the historical first data related to the historical signal and historical information corresponding to the time of the measurement and then determine a set of data associated with the each second subject.

The model generation module 406 may process the sample data. In some embodiments, the model generation module 406 may determine whether a value of a sample data item is abnormal. When a determination is made that a value of a sample data item is abnormal, the set of data associated with the abnormal value is omitted. For example, when a historical blood pressure measurement is identified as a negative value, the model generation module 406 may omit the set of data associated with the abnormal historical blood pressure measurement.

In some embodiments, the model generation module 406 may categorize the sample data and determine a plurality of variables. The plurality of variables may be associated with the time value, the amplitude value, the area value of the characteristic point, the third data related to the representation in the frequency domain, gender, age, height, weight, posture, measured time, historical blood pressure measurement of the second subject, whether or not the second subject is with high blood pressure, whether or not the second subject is under at least one medication, or the like. For the $i^{th}$ variable, the model generation module 406 may use Xi to represent the variable. The plurality of variables may also include a user ID to identify each second subject.

When training or determining one or more models as described below, the model generation module 406 may use at least part of the sample data. The model generation module 406 may determine the one or more models using all of the variables or one or more of the variables (hereinafter referred to as "used variables"). The model generation module 406 may automatically apply data in the sample data corresponding to the used variables and omit data in the sample data corresponding to the unused variables to train or determine the one or more models. The terms "data in the sample data corresponding to the used variables" and "sample data associated with the used variables" may be used interchangeably.

In some embodiments, the model generation module 406 may identify that the relationship between the blood pressure and a first power of a variable is not linear. The model generation module 406 may perform a variable indexation for the variable. In some embodiments, the model generation module 406 may determine a standardized representation associated with the variable such that the standardized relationship between the blood pressure and a first power of the representation is linear. The standardized representation may include an $n^{th}$ (n=2, 3, 4, 5, 6, etc.) power of the variable. For example, the standardized representation associated with a variable Xi may be expressed by Equation (3):

$$F(Xi)=2 \cdot Xi^3+6 \cdot Xi^5 \qquad (3)$$

where Xi may refer to the $i^{th}$ variable. The relationship between the blood pressure and the standardized representation of the $i^{th}$ variable shown in Equation (3) is linear. It should be noted that above description of the representation is for illustrative purpose and not intended to be limiting. The standardized representation may take on other forms based on actual conditions.

The model generation module 406 may randomly divide the sample data into a plurality of sets of first training sample data and testing sample data for a plurality of third predetermined times (e.g., 10 times, 50 times, 100 times, 150 times, etc.). For each of the plurality of third predetermined times, the model generation module 406 may determine a set of first training sample data and testing sample data.

In some embodiments, the first training sample data may correspond to a plurality of sets of data associated with a first group of the plurality of the second subjects. The testing sample data may correspond to a plurality of sets of data associated with a second group of plurality of the second subjects (e.g., the remaining of the plurality of the second subjects). The first training sample data and the testing sample data may correspond to a first percentage of the plurality of the second subjects and a second percentage of the plurality of the second subjects, respectively. For example, the first training sample data may correspond to 10%, 20%, 30%, or 40% of the plurality of second subjects. The testing sample data may correspond to 90%, 80%, 70%, or 60% of the plurality of second subjects. The summation of the first percentage and the second percentage may be equal to or less than 1. It should be understood that the above noted values of the first percentage and the second percentage are for illustrative purpose and not intended to be limiting. The first percentage and the second percentage can be any values between 0 and 1.

In another embodiment, the first training sample data and the testing sample data may include a third portion and a fourth portion of the plurality of sets of data in the sample data, respectively. The first training sample data and the testing sample data may correspond to a third percentage and a fourth percentage of the plurality of sets of data in the sample data, respectively. For example, the third percentage may be any value including 10%, 20%, 30%, 40%, etc. The fourth percentage may be any value including 90%, 80%, 70%, 60%, etc. The summation of the third percentage and the fourth percentage may be equal to or less than 1. It should be noted that each set of data is treated as an entirety during the training and/or testing, and therefore, is indivisible.

In some embodiments, the model generation module 406 may determine the plurality of sets of first training sample data and testing sample data for a plurality of third predetermined times based on cross validation. As a result, the plurality of sets of first training sample data may be associated with each of the plurality of second subjects. The plurality of sets of testing sample data may be associated with each of the plurality of second subjects.

In step 606, the model generation module 406 may generate a preliminary first model for predicting first blood pressure based on the historical first data and the historical information associated with the plurality of second subjects. In some embodiments, the model generation module 406 may generate the preliminary first model based on the sample data, i.e., a combination of the historical first data as described in connection with step 602 and the historical information as described in connection with step 604.

The model generation module 406 may determine the preliminary first model with all of the variables or one or more of the variables as used variables. The preliminary first model may include a random effects model, Bühlmann model, multilevel model, etc. The model generation module 406 may determine a hyperplane based on the sample data associated with the used variables using the preliminary first model in a coordinate system with N+1 dimensions. N may be the number of the used variables. The model generation module 406 may identify the points representing certain sets of data that are far away from the hyperplane. The model generation module 406 may then omit the certain sets of data in the sample data and generate the first sample data. In some embodiments, the model generation module 406 may use the robust regression to omit the certain sets of data for determining the first sample data. Exemplary methods for robust regression may include but not limited to least squares alternatives, parametric alternatives, unit weights, or the like, or a combination thereof. In some embodiments, the model generation module 406 may determine a vector for each set of data in the sample data and determine the hyperplane based on the vectors associated with the plurality of sets of data in the sample data.

In some embodiments, the model generation module 406 may use the first sample data as the input of the preliminary first model to predict first blood pressure. The model generation module 406 may adjust the one or more variables currently used in the preliminary first model, for example, omitting one or more variables from the variables currently in use, adding one or more unused variables into the variables currently in use, or replacing one or more variables currently in use with unused variables. For each time of adjusting the one or more variables, the model generation module 406 may determine information criteria associated with the prediction accuracy and adjust the one or more variables in the preliminary first model.

In some embodiments, the model generation module 406 may use high dimensional variable selection method to adjust the one or more variables in the preliminary first model. For example, the model generation module 406 may use variable selection methods (e.g., stepwise regression, penalty method, etc.) and information criteria to adjust the one or more variables in the preliminary first model. The penalty method may include Lasso, methods related to the Lasso, Smoothly Clipped Absolute Deviation (SCAD), and methods related to the SCAD, etc. The stepwise regression may include but not limited to forward selection, backward elimination, bidirectional elimination, or the like, or a combination thereof. The information criteria may be associated with a difference between the predicted coefficients and actual coefficients. The predicted coefficients may be described below (e.g., the coefficients in Equation (4), the coefficients in Equation (5), etc.). The information criteria may include but not limited to Bayesian information criterion, Akaike information criterion, deviance information criterion, Hannan-Quinn information criterion, or the like, or a combination thereof. The model generation module 406 may determine a plurality of first variables as used variables in the preliminary first model based on the high dimensional variable selection method (e.g., stepwise regression and the information criteria).

In some embodiments, the model generation module 406 may determine a plurality of values of each first variable based on the first training sample data. The model generation module 406 may then determine an average value and a standard deviation of the each first variable. The standard deviation may indicate dispersion degree associated with the plurality of values of the each first variable. For each value of the each first variable, the model generation module 406 may subtract the average value from the each value to determine a difference. The model generation module 406 may then divide the difference by the standard deviation to determine a standardized value associated with the each first variable.

The model generation module 406 may determine second training sample data based on the standardized values associated with the first variables and the first training sample data. In some embodiments, the model generation module 406 may determine the second training sample data by replacing the plurality of values associated with the first variables in the first training sample data with the standardized values associated with the first variables.

The model generation module 406 may determine a hyperplane based on the second training sample data using the preliminary first model with the plurality of first variables as used variables. The model generation module 406 may then determine a relationship between the first blood pressure and the first variables. For example, the relationship may be expressed by Equation (4):

$$F1=q_1 f(X1)+q_2 f(X2)+ \ldots +q_m f(Xm) \quad (4)$$

where F1 may refer to a parameter associated with the first blood pressure, coefficient $q_i$ (i=1, 2, . . . , m) may refer to the coefficient corresponding to the $i^{th}$ first variable, f(Xi) may refer to a representation of the $i^{th}$ first variable, m may refer to the number of the first variables. In some embodiments, the parameter associated with the first blood pressure may be a diastolic pressure, a systolic pressure, a blood pressure difference, an average blood pressure, a logarithm thereof, or the like, or a combination thereof. In some embodiments, f(Xi) may be a first power of the $i^{th}$ first variable (i.e., f(Xi)=Xi), or an $n^{th}$ power of the $i^{th}$ first variable. In some embodiments, f(Xi) may include a standardized representation associated with the variable Xi (e.g., Equation (3)).

The model generation module 406 may rank the coefficients $q_i$ based on their values. The model generation module 406 may identify a first coefficient with the minimum value. The model generation module 406 may omit the first variable associated with the first coefficient and determine a plurality of second variables as used variables.

The model generation module 406 may then determine the preliminary first model based on the plurality of second variables. For each set of data in the testing sample data, the model generation module 406 may determine a first blood pressure value. The model generation module 406 may determine a residual between the first blood pressure value and the corresponding historical blood pressure measurement. Generally, the residual associated with the predicted first blood pressure value may refer to the difference between the measured value (e.g., the historical blood pressure measurement) and the predicted value (e.g., the predicted first blood pressure value) associated with each set of data. The model generation module 406 may determine a first average value of a plurality of the residuals associated with the sets of data in the testing sample data.

The model generation module 406 may successively omit a variable associated with a coefficient with the second minimum value, and then successively omit a variable associated with a coefficient with the third minimum value, or the like. For each time of omitting a variable, the model generation module 406 may determine an average value associated with the residuals. The model generation module 406 may determine the minimum average value and identify the remaining variables corresponding to the minimum average value. The model generation module 406 may determine the remaining variables as a plurality of third variables (also referred to "used variables"). Referring to Equation (4), the model generation module 406 may determine the preliminary first model based on the first sample data associated with the plurality of third variables (also referred to as "the used preliminary first model") expressed by Equation (5):

$$F1=q_1 f(X1)+q_2 f(X2)+ \ldots +q_1 f(Xj) \quad (5)$$

where j may be the number of the plurality of third variables, and the values of coefficient $q_i$ (i=1, 2, . . . , j) may be different from the values in Equation (4).

For each set of data in the sample data (e.g., the first training sample data, the testing sample data, etc.) associated with the plurality of third variables, the model generation module 406 may determine the first blood pressure value based on the used preliminary first model (e.g., Equation (5)). The model generation module 406 may determine a residual between the first blood pressure and the corresponding historical blood pressure measurement. The model generation module 406 may designate this residual as an actual residual. The model generation module 406 may determine a plurality of actual residuals related to the sets of data in the sample data associated with the plurality of third variables.

In some embodiments, the model generation module 406 may further determine a plurality of sub-models. Each sub-model may be associated with a specific condition. The specific condition may be associated with a group of second subjects classified by an age range, a posture of measurement of a second subject, time of measurement, a season of measurement, or an interaction with at least part of the specific conditions described above, etc. In some embodiments, the age range may include but not limited to 0-5 years old, 5-12 years old, 12-18 years old, 18-30 years old, 30-45 years old, 45-60 years old, 60-80 years old, or the like, or a combination thereof. The age range may include any other length of age separations. The posture of measurement may include lying, sitting, standing, etc. In some embodiments, the time of measurement may include morning, afternoon, night, etc. The time of measurement may also include a plurality of time intervals. For example, the time interval may be 6 a.m.-9 a.m., 6 a.m.-12 a.m., 12 a.m.-6 p.m., 6 p.m.-12 p.m., 12 p.m.-6 a.m., or the like. The plurality of time intervals may include any other length of time intervals. The season of measurement may include spring, summer, autumn, and winter. The season of measurement may also include a plurality of spans of months. The span of months may include from January to February, from February to May, from April to June, from June to September, from October to December, etc. The season of measurement may include any other spans of months during one year or cross several years. The specific condition may be default settings or adjusted in different situations. It should be understood that the specific conditions described above are for illustrative purpose. The present disclosure is not intended to be limiting. The specific condition may be determined to construct the group of second subjects based on different countries, different climates, different regions, different altitudes, different races, different genders, different occupations, different education levels, different pre-existing conditions, different drug records, or the combination thereof. The interaction with at least part of the specific conditions described above may include interaction terms between the historical signals associated with the plurality of second subjects, determination as to whether a second subject is diagnosed high blood pressure, or the like.

The model generation 406 may determine the plurality of sub-models based on the method for determining the preliminary first model as described above. The model generation 406 may determine the plurality of sub-models based on the data for determining the preliminary first model as described above. And data for determining the plurality of sub-models may be further associated with a specific condition of a sub-model.

In step 608, the model generation module 406 may generate a preliminary second model for predicting a plurality of residuals between the plurality of historical blood pressure measurements and the first blood pressure values predicted by the used preliminary first model based on the historical first data and the historical information associated with the plurality of second subjects. The model generation module 406 may determine the preliminary second model with all of the variables or one or more of the variables as used variables. The model generation module 406 may determine the preliminary second model for predicting a plurality of residuals associated with a group of second subjects. The group of second subjects may include but not limited to second subjects with high blood pressures, second subjects in senior ages, or the like, or a combination thereof.

In some embodiments, used variables in the preliminary second model may include the entire variables. In another embodiment, used variables in the preliminary second model may include one or more of the entire variables. The model generation module 406 may determine a portion of the calibration sample data corresponding to a group of second subjects (e.g., the second subjects with high blood pressures, the second in senior ages, etc.) as input of the preliminary second model. As described in connection with step 606, the model generation module 406 may determine which variables may be used in the preliminary second model based on the portion of the calibration sample data, the high dimensional variable selection method (e.g., the stepwise regression and the information criterion). The model generation module 406 may determine a plurality of fourth variables as used variables in the preliminary second model and then determine the preliminary second model (also referred to as "the used preliminary second model") expressed as Equation (6):

$$F2 = p_1 \cdot f(X1) + p_2 \cdot f(X2) + \ldots + p_k \cdot f(Xk) \quad (6)$$

Where F2 may refer to the predicted residual, coefficient $p_i$ (i=1, 2, . . . , k) may refer to the coefficient corresponding to the $i^{th}$ fourth variable, f(Xi) may refer to a representation of the $i^{th}$ fourth variable, k may be the number of the fourth variables. For example, f(Xi) may be a first power of the $i^{th}$ fourth variable (i.e., f(Xi)=Xi), or an $n^{th}$ power of the $i^{th}$ fourth variable. In some embodiments, f(Xi) may include a standardized representation associated with the fourth variable.

In some embodiments, the model generation module 406 may determine the prediction accuracy associated with the used preliminary second model. The model generation module 406 may determine the calibration testing sample data. The calibration testing sample data may be the calibration sample data directed to the second subjects associated with the testing sample data. For each set of data in the calibration testing sample data, the model generation module 406 may determine a predicted residual associated with the each set of data based on the used preliminary second model. The model generation module 406 may determine a plurality of predicted residuals accordingly. The model generation module 406 may determine the prediction accuracy associated with the used preliminary second model based on the plurality of predicted residuals and the plurality of actual residuals. Step 608 may be performed iteratively until the prediction accuracy reaches a predetermined threshold.

It should be noted that the used preliminary second model may be used for correcting the first blood pressure associated a group of second subjects (e.g., the second subjects with high blood pressures, the second subjects in senior ages, etc.) by adding the corresponding residual to the corresponding first blood pressure or by subtracting the corresponding residual from the corresponding first blood pressure.

In step 610, the model generation module 406 may determine a preliminary model for predicting blood pressure based on the used preliminary first model, the plurality of sub-models, the used preliminary second model and the historical information associated with the plurality of second subjects. In some embodiments, for determining the preliminary model, the model generation module 406 may determine a preliminary third model. The preliminary third model may be a combination of the used preliminary first model, the plurality of sub-models, and the used preliminary second model. The model generation module 406 may select one or more sub-models (also referred to as "the selected sub-models") to determine the preliminary third model. The model generation module 406 may determine a weighted coefficient for each of the used preliminary first model, the selected sub-models, and the used preliminary second model based on the first training sample data. The model generation module 406 may use the random forest model and the deep learning method to determine the each weighted coefficient. In some embodiments, the model generation model 406 may determine that the preliminary model is further associated with at least part of variables in the historical information.

In some embodiments, the model generation module 406 may determine a hyperplane using the first training sample data associated with used variables of the preliminary third model based on the preliminary third model in a coordinate system. The number of dimensions of the coordinate system may be a summation of the number of the used variables herein (e.g., the third variables and/or fourth variables) and 1. The model generation module 406 may determine the values of the weighted coefficients based on the hyperplane.

The model generation module 406 may determine a random forest model. The random forest model may include an ensemble learning method for classification, regression, or the like. The algorithms of the random forest model may include but not limited to decision tree learning, tree bagging ExtraTrees, or the like, or a combination thereof. In some embodiments, the random forest model may include a plurality (e.g., 100, 200, 250, 400, 500, 600, etc.) of decision trees. The algorithm of a decision tree may include an iterative dichotomiser 3 algorithm, classification and regression tree algorithm, successor of ID3 algorithm, CHi-squared automatic interaction detector algorithm, conditional inference trees algorithm, or the like, or any combination thereof.

The model generation module 406 may determine the at least part of variables in the historical information based on the random forest model and/or the deep learning method. The model generation module 406 may determine the preliminary model based on the preliminary third model and the at least part of variables of the historical information.

In step 612, the model generation module 406 may generate a personalized model for predicting blood pressure with respect to a second subject based on the used preliminary first model for predicting blood pressure, the selected sub-models, the used preliminary second model, the historical first data with respect to the second subject, and at least part of the historical information with respect to the first subject. The at least part of the historical information may correspond to the at least part of variables in the historical information associated with the preliminary model. In some embodiments, the model generation module 406 may use the calibration testing sample data to determine the personalized model for predicting blood pressure.

As described in connection with step 604, the model generation module 406 may determine the plurality of sets of first training sample data and testing sample data. The model generation module 406 may use the plurality of sets of first training sample data and testing sample data to determine the used preliminary first model, the plurality of sub-models, the used preliminary second model, the preliminary model and the personalized model. For each of the plurality of second subjects, the model generation module 406 may determine a personalized model. In some embodiments, the model generation module 406 may further use cross validation to determine the used preliminary first model, the plurality of sub-models, the used preliminary second model, and the preliminary model. In some embodiments, the sample data and the calibration sample data may be updated with time. Accordingly, the model generation module 406 may update the used preliminary first model, the used preliminary second model, the plurality of sub-models, and the preliminary model.

For each second subject, the model generation module 406 may determine the personalized first model and the personalized second model based on the used preliminary first model and the used preliminary second model using the calibration testing sample data associated with the each second subject, respectively. For example, for determining the personalized first model and the personalized second model associated with each second subject, the model generation module 406 may update the coefficients in the used preliminary first model (e.g., Equation (5)) and the used preliminary second model (e.g., Equation (6)) based on the sample data associated with the each second subject.

In some embodiments, the model generation 406 may determine the selected sub-models associated with the personalized model from the plurality of sub-models. The model generation 406 may then determine personalized selected sub-models based on the calibration testing sample data.

The model generation module 406 may determine the personalized model for predicting blood pressure with respect to each second subject based on the corresponding personalized first model, the corresponding personalized second model, the corresponding personalized selected sub-models, and the at least part of historical information. For example, the model generation module 406 may update the weighted coefficients in the preliminary model (e.g., the preliminary third model) to determine the personalized model. The model generation module 406 may use the ubiquitous computing (also referred to as "the wearable computing") to determine the personalized model. In some embodiments, the model generation module 406 may use the statistical iterative updating and/or Bayesian posterior predictive updating to determine the personalized model. The ubiquitous computing may be implemented by the measuring device 110 (e.g., by incorporating one or more computer chips) and/or the terminal 140 (e.g., an application). In some embodiments, the calibration sample data associated with a second subject may be updated with time. Accordingly, the model generation module 406 may update the personalized model. The updating method may be also the ubiquitous computing, the statistical iterative updating and/or Bayesian posterior predictive updating.

In some embodiments, for predicting blood pressure of a third subject not included in the plurality of second subjects, the model generation module 406 may obtain calibration sample data associated with the third subject. The model generation module 406 may generate personalized model for predicting blood pressure of the third subject based on the sample data associated with the third subject.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment," "one embodiment," or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "block," "module," "engine," "unit," "component," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 1703, Perl, COBOL 1702, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a software as a service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in less than all features of a single foregoing disclosed embodiment.

What is claimed is:

1. A system for determining blood pressure, comprising:
   at least one storage medium including a set of instructions;
   a communication platform connected to a network; and
   at least one processor configured to communicate with the at least one storage medium, wherein when executing the set of instructions, the at least one processor is directed to:
      receive a request to determine a blood pressure of a first subject from a terminal;
      obtain data related to a heart activity of the first subject in response to the request;
      determine a personalized model for predicting blood pressure with respect to the first subject;
      determine the blood pressure of the first subject using the personalized model based on the data related to the heart activity of the first subject; and
      send the blood pressure of the first subject to the terminal in response to the request;
   wherein to determine the personalized model for predicting blood pressure with respect to the first subject, the at least one processor is further directed to:
      obtain historical data related to heart activities of a plurality of second subjects, wherein the plurality of second subjects includes the first subject, and the historical data includes a plurality of historical blood pressure measurements with respect to the plurality of second subjects;
      generate a first model for predicting first blood pressure based on the historical data related to the heart activities of the plurality of second subjects;
      generate a second model for predicting a plurality of residuals between the plurality of historical blood pressure measurements and values of the first blood pressure predicted by the first model based on the historical data related to the heart activities of the plurality of second subjects:
      determine a preliminary model for predicting blood pressure based on the first model, the second model, and at least part of the historical data related to the heart activities of the plurality of second subjects; and
      generate the personalized model for predicting blood pressure with respect to the first subject based on the preliminary model for predicting blood pressure and at least part of historical data related to the heart activity of the first subject.

2. The system of claim 1, wherein to obtain the data related to the heart activity of the first subject, the at least one processor is further directed to:
   communicate with a sensor attached to the first subject, the sensor being configured to detect the heart activity of the first subject and generate a signal; and
   generate the data related to the heart activity of the first subject based on the signal.

3. The system of claim 1, wherein the data related to the heart activity of the first subject includes at least one of
   the age of the first subject,
   gender of the first subject,
   height of the first subject,
   weight of the first subject,
   posture of the first subject,
   time information associated with the request,
   whether or not the first subject has high blood pressure, or
   whether or not the first subject is under at least one medication.

4. The system of claim 2, wherein to generate the data related to the heart activity of the first subject based on the signal, the at least one processor is further directed to:
- transform the signal into a first representation in the frequency domain;
- determine a first plurality of coefficients related to the first representation in the frequency domain; and
- generate the data related to the heart activity of the first subject based on the first plurality of coefficients.

5. The system of claim 2, wherein to generate the data related to the heart activity of the first subject based on the signal, the at least one processor is further directed to:
- transform a portion of the signal into a second representation in the frequency domain;
- determine a second plurality of coefficients related to the second representation in the frequency domain; and
- generate the data related to the heart activity of the first subject based on the second plurality of coefficients.

6. A method for determining blood pressure implemented on a computing device having at least one processor, at least one storage medium, and a communication platform connected to a network, the method comprising:
- receiving a request to determine a blood pressure of a first subject from a terminal;
- obtaining data related to a heart activity of the first subject in response to the request;
- determining a personalized model for predicting blood pressure with respect to the first subject;
- determining the blood pressure of the first subject using the personalized model based on the data related to the heart activity of the first subject; and
- sending the blood pressure of the first subject to the terminal in response to the request;
- wherein the determining the personalized model for predicting blood pressure with respect to the first subject further comprises:
  - obtaining historical data related to heart activities of a plurality of second subjects, wherein the plurality of second subjects includes the first subject, and the historical data includes a plurality of historical blood pressure measurements with respect to the plurality of second subjects;
  - generating a first model for predicting first blood pressure based on the historical data related to the heart activities of the plurality of second subjects;
  - generating a second model for predicting a plurality of residuals between the plurality of historical blood pressure measurements and values of the first blood pressure predicted by the first model based on the historical data related to the heart activities of the plurality of second subjects;
  - determining a preliminary model for predicting blood pressure based on the first model, the second model, and at least part of the historical data related to the heart activities of the plurality of second subjects; and generating the personalized model for predicting blood pressure with respect to the first subject based on the preliminary model for predicting blood pressure and at least part of historical data related to the heart activity of the first subject.

7. The method of claim 6, wherein the obtaining the data related to the heart activity of the first subject comprises:
- communicating with a sensor attached to the first subject, the sensor being configured to detect the heart activity of the first subject and generate a signal; and
- generating the data related to the heart activity of the first subject based on the signal.

8. The method of claim 6, wherein the data related to the heart activity of the first subject includes at least one of
- the age of the first subject,
- gender of the first subject,
- height of the first subject,
- weight of the first subject,
- posture of the first subject,
- time information associated with the request,
- whether or not the first subject has high blood pressure, or
- whether or not the first subject is under at least one medication.

9. The method of claim 7, wherein the generating the data related to the heart activity of the first subject based on the signal further comprises:
- transforming the signal into a first representation in the frequency domain;
- determining a first plurality of coefficients related to the first representation in the frequency domain; and
- generating the data related to the heart activity of the first subject based on the first plurality of coefficients.

10. The method of claim 7, wherein the generating the data related to the heart activity of the first subject based on the signal further comprises:
- transforming a portion of the signal into a second representation in the frequency domain;
- determining a second plurality of coefficients related to the second representation in the frequency domain; and
- generating the data related to the heart activity of the first subject based on the second plurality of coefficients.

11. A system for determining blood pressure, comprising:
- at least one storage medium including a set of instructions;
- a communication platform connected to a network; and
- at least one processor configured to communicate with the at least one storage medium, wherein when executing the set of instructions, the at least one processor is directed to:
- receive a request to determine a blood pressure of a first subject from a terminal;
- obtain data related to a heart activity of the first subject in response to the request;
- send the data related to the heart activity of the first subject to a cloud server;
- receive the blood pressure of the first subject determined by the cloud server, wherein the blood pressure of the first subject is determined by performing:
  - determining a personalized model for predicting blood pressure with respect to the first subject, wherein the personalized model is determined by performing the following steps:
    - obtain historical data related to heart activities of a plurality of second subjects, wherein the plurality of second subjects includes the first subject, and the historical data includes a plurality of historical blood pressure measurements with respect to the plurality of second subjects;
    - generate a first model for predicting first blood pressure based on the historical data related to the heart activities of the plurality of second subjects;
    - generate a second model for predicting a plurality of residuals between the plurality of historical blood pressure measurements and values of the first blood pressure predicted by the first model based on the historical data related to the heart activities of the plurality of second subjects;
    - determine the preliminary model for predicting blood pressure based on the first model, the second model, and at least part of the historical data related to the heart activities of the plurality of second subjects; and generate the personalized model for predicting blood pressure with respect to the first subject based on the preliminary model for predicting blood pressure and at least part of historical data related to the heart activity of the first subject;

determining a blood pressure of the first subject using the personalized model based on the data related to a heart activity of the first subject; and send the blood pressure of the first subject to the terminal in response to the request.

12. The system of claim 11, wherein to obtain the data related to the heart activity of the first subject, the at least one processor is further directed to:

communicate with a sensor attached to the first subject, the sensor being configured to detect the heart activity of the first subject and generate a signal; and generate the data related to the heart activity of the first subject based on the signal.

13. The system of claim 11, wherein the data related to heart activity of the first subject includes at least one of the age of the first subject,
gender of the first subject,
height of the first subject,
weight of the first subject,
posture of the first subject,
time information associated with the request,
whether or not the first subject has high blood pressure, or
whether or not the first subject is under at least one medication.

14. The system of claim 12, wherein to generate the data related to the heart activity of the first subject based on the signal, the at least one processor is further directed to:

transform the signal into a first representation in the frequency domain;

determine a first plurality of coefficients related to the first representation in the frequency domain; and generate the data related to the heart activity of the first subject based on the first plurality of coefficients.

15. The system of claim 12, wherein to generate the data related to the heart activity of the first subject based on the signal, the at least one processor is further directed to:

transform a portion of the signal into a second representation in the frequency domain;

determine a second plurality of coefficients related to the second representation in the frequency domain; and generate the data related to the heart activity of the first subject based on the second plurality of coefficients.

* * * * *